US010405804B2

(12) United States Patent
Al-Ali

(10) Patent No.: US 10,405,804 B2
(45) Date of Patent: *Sep. 10, 2019

(54) PHYSIOLOGICAL MEASUREMENT LOGIC ENGINE

(71) Applicant: Masimo Corporation, Irvine, CA (US)

(72) Inventor: Ammar Al-Ali, San Juan Capistrano, CA (US)

(73) Assignee: Masimo Corporation, Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/634,745

(22) Filed: Jun. 27, 2017

(65) Prior Publication Data
US 2017/0332976 A1 Nov. 23, 2017

Related U.S. Application Data

(63) Continuation of application No. 14/967,075, filed on Dec. 11, 2015, now Pat. No. 9,693,737, which is a continuation of application No. 13/425,085, filed on Mar. 20, 2012, now Pat. No. 9,211,095, which is a continuation of application No. 13/272,038, filed on Oct. 12, 2011, now abandoned.

(60) Provisional application No. 61/392,863, filed on Oct. 13, 2010.

(51) Int. Cl.
A61B 5/1455 (2006.01)
A61B 5/00 (2006.01)
A61B 7/02 (2006.01)

(52) U.S. Cl.
CPC .......... A61B 5/7271 (2013.01); A61B 5/0059 (2013.01); A61B 5/1455 (2013.01); A61B 5/14551 (2013.01); A61B 5/7264 (2013.01); A61B 5/7282 (2013.01); A61B 5/742 (2013.01); A61B 5/746 (2013.01); A61B 7/02 (2013.01)

(58) Field of Classification Search
CPC ... A61B 5/7271; A61B 5/0059; A61B 5/1455; A61B 5/14551; A61B 5/7264; A61B 5/7282; A61B 5/742; A61B 5/746
See application file for complete search history.

(56) References Cited

U.S. PATENT DOCUMENTS

| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |

(Continued)

OTHER PUBLICATIONS

US 8,845,543 B2, 09/2014, Diab et al. (withdrawn)

Primary Examiner — Eric F Winakur
(74) Attorney, Agent, or Firm — Knobbe, Martens, Olson & Bear, LLP

(57) ABSTRACT

A patient monitor including a physiological measurement logic engine receives physiological data from a physiological sensor. The logic engine abstracts one or more features of the physiological data and determines a category for the abstracted feature. The logic engine further encodes the category of each of the one or more features and determines an action to perform based on the encoded categories.

20 Claims, 9 Drawing Sheets

(56) References Cited

U.S. PATENT DOCUMENTS

| | | |
|---|---|---|
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |

(56) References Cited

U.S. PATENT DOCUMENTS

| | | | |
|---|---|---|---|
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,209,774 | B2 | 4/2007 | Baker, Jr. |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al Ali et al. |
| 7,377,899 | B2 | 5/2008 | Weber et al. |
| 7,383,070 | B2 | 6/2008 | Diab et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,526,328 | B2 | 4/2009 | Diab et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,596,398 | B2 | 9/2009 | Al-Ali et al. |
| 7,618,375 | B2 | 11/2009 | Flaherty |
| D606,659 | S | 12/2009 | Kiani et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,706,852 | B2 | 4/2010 | Baker, Jr. |
| RE41,317 | E | 5/2010 | Parker |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Al-Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |

(56) References Cited

U.S. PATENT DOCUMENTS

| | | |
|---|---|---|
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |

(56) References Cited

U.S. PATENT DOCUMENTS

| | | |
|---|---|---|
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,211,095 B1 | 12/2015 | Al-Ali |
| 9,693,737 B2 | 7/2017 | Al-Ali |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0303520 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

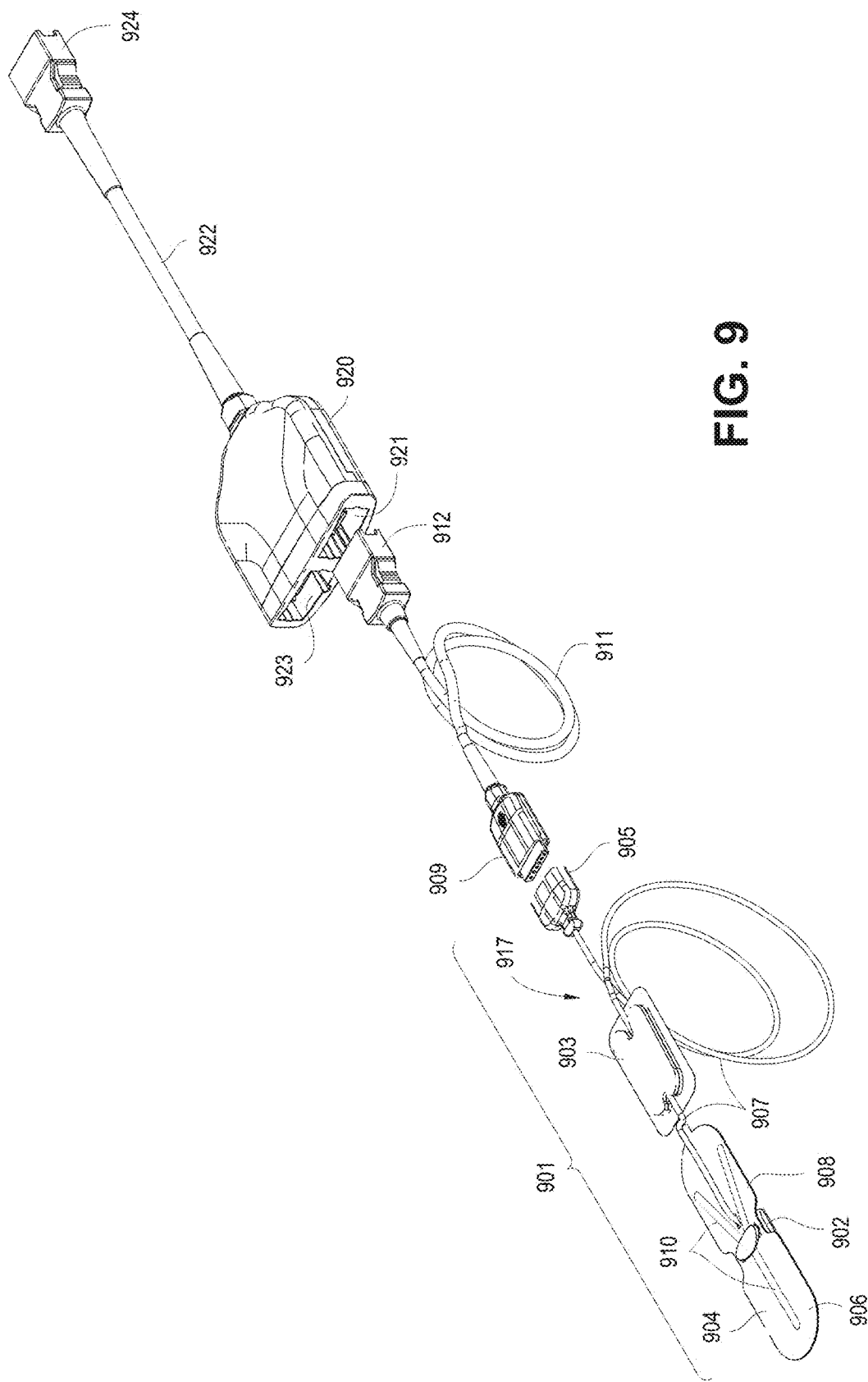

PHYSIOLOGICAL MEASUREMENT LOGIC ENGINE

RELATED APPLICATIONS

The present application is a continuation of U.S. patent application Ser. No. 14/967,075, filed Dec. 11, 2015, entitled "Physiological Measurement Logic Engine," now U.S. Pat. No. 9,693,737, which is a continuation of U.S. patent application Ser. No. 13/425,085, filed Mar. 20, 2012, entitled "Physiological Measurement Logic Engine," now U.S. Pat. No. 9,211,095, which is a continuation of U.S. patent application Ser. No. 13/272,038, filed Oct. 12, 2011, entitled "Physiological Measurement Logic Engine," which claims priority benefit of U.S. Provisional Patent Application No. 61/392,863, filed Oct. 13, 2010, entitled "Physiological Measurement Logic Engine," each of which is hereby incorporated by reference herein in its entirety.

FIELD

The present disclosure relates to non-invasive biological parameter sensing, including sensing using optical and/or acoustic sensors and related systems and methods.

BACKGROUND

Patient monitoring of various physiological parameters of a patient is important to a wide range of medical applications. Pulse oximetry is one of the techniques that have developed to accomplish the monitoring of some of these physiological characteristics. Pulse oximetry relies on a sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate.

High fidelity patient monitors capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter. Advanced physiological monitors and multiple wavelength optical sensors capable of measuring parameters in addition to SpO2, such as HbCO, HbMet and/or Hbt are described in at least U.S. patent Ser. No. 11/367,013, filed Mar. 1, 2006, titled Multiple Wavelength Sensor Emitters, now issued as U.S. Pat. No. 7,764,982, and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp. of Irvine, Calif.

Another physiological monitoring system uses sensors that include piezoelectric membranes located on or near a patient's body to measure body sounds. The body sounds can then be analyzed to determine ventilation, apnea, respiration rate, or other parameters. These monitors are referred to as acoustic respiratory monitors. Acoustic respiratory monitors are also commercially available from Masimo Corp. of Irvine, Calif.

SUMMARY

The present disclosure relates to a system for simplifying logic choices in a computing environment. In an embodiment physiological processing is simplified by abstracting relevant features, or general characteristics of the signal. As used herein, features and general characteristics are used interchangeably. In an embodiment, features of physiological signals are abstracted and are used in conjunction with a logic table in order to determine a course of action. In an embodiment, the abstracted features are used to provide a bit encoding scheme which directly relates to a specified result. In an embodiment, the system is used to encode logic choices relevant to display characteristics of the device.

BRIEF DESCRIPTION OF THE DRAWINGS

FIG. 9 illustrates an embodiment of an acoustic sensor system, which can provide physiological data to the patient monitoring system.

DETAILED DESCRIPTION

Signal Analysis

Figure 1:
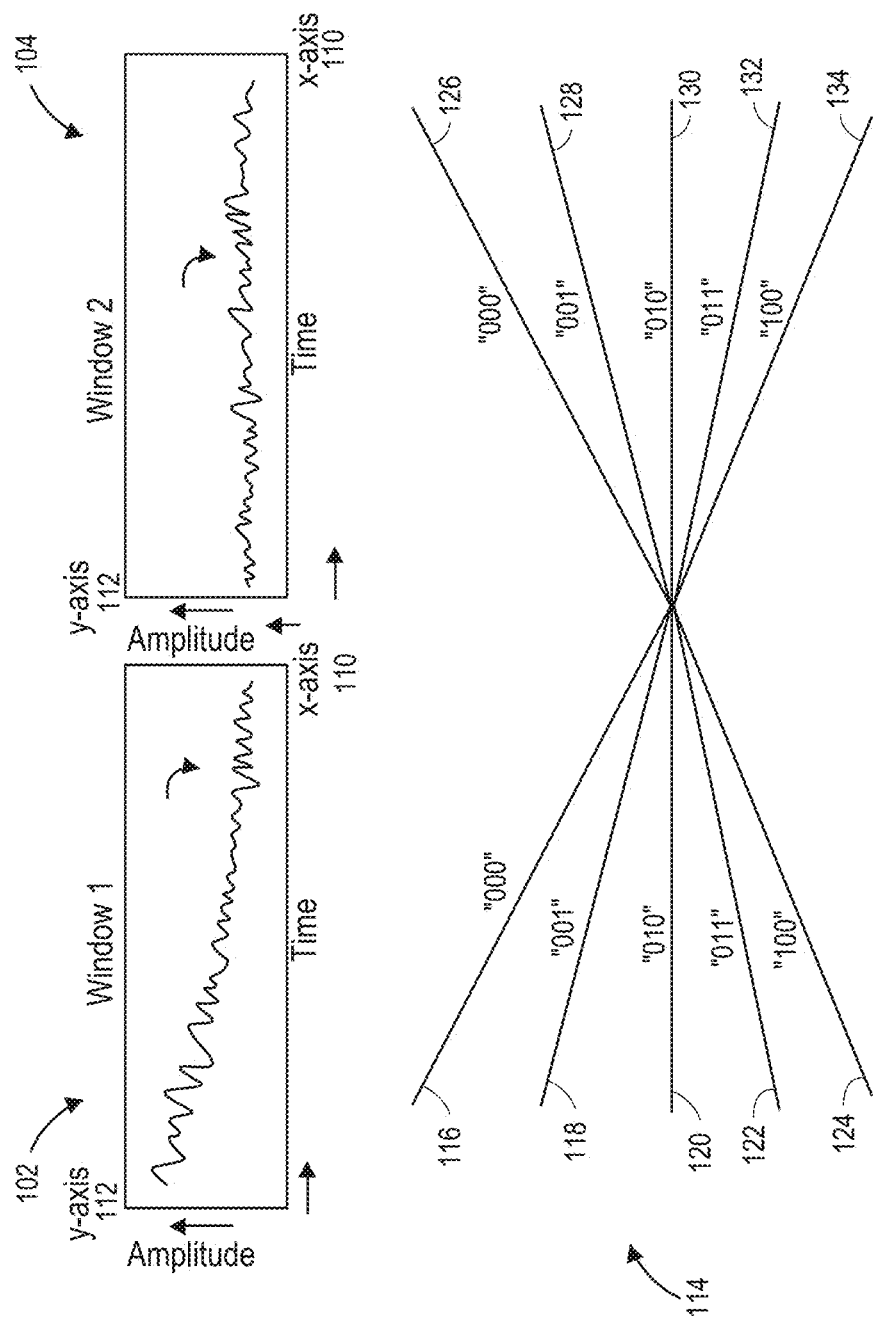
FIG. 1 illustrates an example of an abstraction of the relative slopes of physiological signals.

Real time processing of physiological signals is often difficult and requires significant computing power, fast processors and significant power consumption and heat dissipation. Typical signal processing involves intensive and difficult mathematic operations in order to extrapolate useful data.

Feature Abstraction

One way to reduce the computational load in a physiological processing system is to abstract features of the signal. Feature abstractions use only relatively simple analysis which significantly reduces computational loads. Once abstracted, the features can then be used to make determinations about the physiological signals.

The difference between feature abstraction and typical computationally intensive signal processing is best understood with an analogy to human observations vs. computations. For example, consider the situation where Person A lives next to Person B. Person B brings their trash container out to the same position every time the trash is collected. Although Person A may not consciously note the position of the trash container, Person A is likely to notice that something is different if the trash container is placed in a different position. Importantly, that recognition can be made without measuring the exact position change of the trash container or even consciously noting the normal position of the trash container. Similarly, Person A may further note other changes regarding Person B. For example, Person A is likely to note that a different car is parked in Person B's driveway. Person A can make this determination without comparing old and new license plate numbers. Another example may be that Person A notes different children playing in Person B's yard. None of these abstractions or general observations required significant thought or specific measurements on the part of Person A. Similarly, features of physiological signals can be abstracted at various levels without significant computations.

Once abstracted, each feature can potentially indicate a number of possible explanations. For example, using the same analogy above, the change in location of Person B's trash container could indicate that a different family member took out the trash. However, coupling the change in location of trash container along with the different car and unfamiliar children playing in the yard may indicate that Person A has new neighbors. Importantly, the conclusion that Person A may have new neighbors is made without having direct knowledge of a change in neighbors or actually seeing the neighbors. Similarly, combinations of abstracted features provide different indications about the signal under analysis, while using relatively low processing power. However, it is to be understood that abstracting features of the signals described herein is significantly more complex and computationally intensive than the example given above. Furthermore, the abstraction of features of the signals (or data) described herein is typically done in real-time or near real-time using a digital signal processor, microcontroller, or other processor, operating at speeds far surpassing those of a human. For example, the processor may operate at hundreds, thousands, millions, billions, or even more cycles per second to ensure the features are abstracted in a timely manner. If the features are abstracted too slowly they lose their relevance.

In an embodiment, various features of a detected signal are abstracted. For example, in an embodiment, the relative slope of a signal over one or more windows of time is abstracted. In an embodiment, the relative noise level of a signal is determined. In an embodiment, the relative signal strength is determined. In an embodiment, comparisons between various features over different windows of time are compared and the comparison is an abstracted feature. In an embodiment, the features are abstracted in real-time or near real-time. Other abstractions can also be made as will be understood by those of skill in the art based on the present disclosure.

Figure 2:
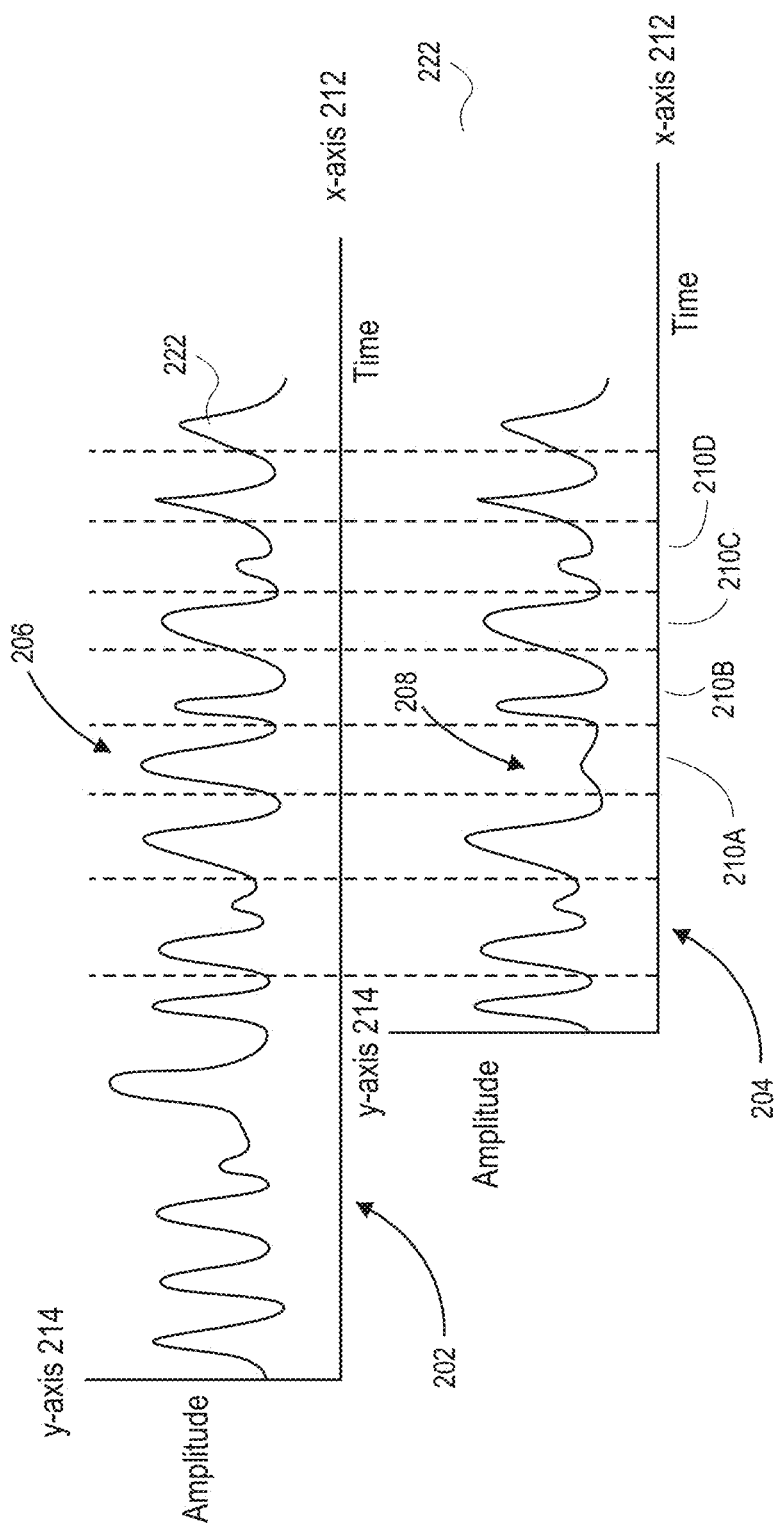
FIG. 2 illustrates an example of an abstraction of the difference in outputs of different processing engines.
Figure 3:
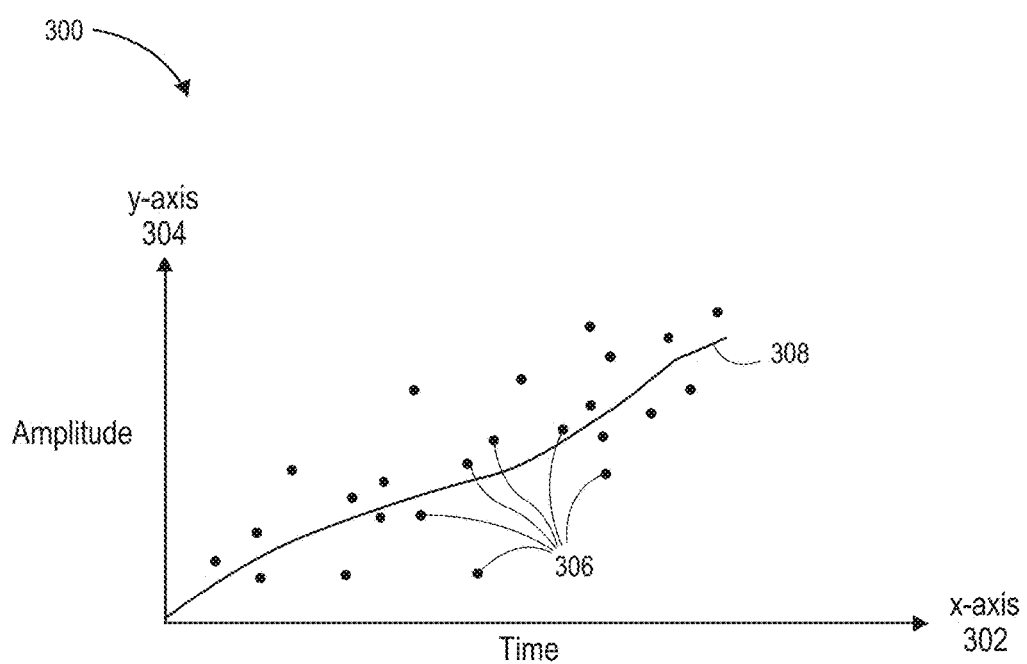
FIG. 3 illustrates an example of an abstraction of a trend line linear regression, and/or a standard deviation.

The examples provided below in FIGS. 1-3 are simplified examples of the types of abstractions that occur using the device described herein. It is to be understood that the calculations, computations, and abstractions are performed in real-time or near real-time at speeds surpassing those capable of a human. For example, the processor may perform hundreds, thousands, millions, billions or more calculations per second to determine the appropriate abstraction in real time or near real-time. In addition, the signals (or data) abstracted by the processor may be electrical signals, infrared signals, wireless signals, or other electro-magnetic wave signals that are incomprehensible to a human in their raw form and at the speeds communicated.

FIG. 1 illustrates an example of an abstraction of the relative slopes of physiological signals. As illustrated in FIG. 1, signals within two windows of time 102, 104 are analyzed. The windows can be any length of time. In an embodiment, each window is 30 seconds long. In another embodiment, each window is 60 seconds long. Other lengths of time can also be used. The windows can overlap or be non-overlapping in time. The signals in each window are then abstracted and characterized into one of five different slopes. These slopes are illustrated by the slope abstraction illustrator 114. For example, the relative slope of the signal within window 102 most closely matches slope 118. Similarly, the overall slope of the signal, or data, within window 104 most closely matches slope 130. By abstracting the overall slope of the signal into a relative slope, computations relevant to the signals are simplified. The overall slope of the signal may also be referred to as the trend of the signal. Although described with respect to five different slope abstraction values, more or fewer abstractions levels can be used. For example, one system might use 10 different abstraction slopes while another system might use three different abstraction slopes.

In an embodiment, after abstraction, the signal in each window is assigned a category. In the embodiment illustrated, the category is a bit code corresponding to the slope abstraction. In an embodiment, the slope of the signal in window 102, is matched to slope 118, and assigned bits "001." Similarly, the slope of the signal in window 104 is assigned to bits "010." As will be explained in greater detail below, bit assignments can be used to further simplify processing. Furthermore, as will be understood by those in the art from the present disclosure, the bit codes presented in the this example are not intended to be limiting and other bit codes, including different numbers of bits, can be used with the present disclosure.

In an embodiment, after abstracting the slopes of two or more signals in two or more windows of time, the slopes are then compared in order to determine a change in slope. The change in relative slope then provides another abstraction that can be used in further processing to make determinations regarding the signal. In an embodiment, this abstraction is also assigned a bit code based on the comparison. In an embodiment, the comparison is not necessary because the bit codes can be used in conjunction with the table described in FIG. 4 to designate an outcome based on the slopes without the necessity of further comparison computations. Thus, as described below, using the bit codes in association with FIG. 4 obviates the need the further processing and computational steps that might otherwise be necessary.

Another abstraction involves the comparison of two overlapping windows of data. This is illustrated, for example, in FIG. 2. Typically, physiological signals received from sensors are processed before being displayed. In processing the physiological signals, a patient monitor, described in more detail below with reference to FIGS. 7 and 9, performs any number of functions, computations, filters, and the like. The processing can account for signal noise, motion artifact, or any number of other signal distortions that can affect signal quality and the reliability of the output.

In an embodiment a patient monitor processes the data using one or more processing techniques, which may also be referred to as engines or processing engines, in parallel. The various engines can identify and filter specific signal distortions. For example, one engine can be configured to filter according to repetitive motion, while another engine can be configured to filter according to a single instance of motion. Other engines may be configured to filter or process the signals to account for other signal distortions, such as low signal-to-noise ratio, low signal power, low perfusion and the like. The use of parallel engines is described in U.S. Pat. No. 6,157,850, the disclosure of which is hereby incorporated by reference in its entirety.

With continued reference to FIG. 2, window 202 is an illustration of a physiological signal processed over a first time period, or window of time. Window 204 is an illustration of the same physiological signal processed over a different window of time, but that overlaps with the first window of time. This can be done using the same or different engines for each window of time. The x-axis 212 of the windows 202, 204 represents time, and the y-axis 214 of the windows 202, 204 represents signal amplitude. The data 220, 222 can be any type of physiological data, signal, or other data. Furthermore, the windows 202, 204 can be broken down into time the segments 210A, 210B, 210C, 210D, that divide the data based on a predefined time period. The predefined time period may be any size, ranging from less than a microsecond to minutes, hours or more. Typically, the data within the same time segments 210A, 210B, 210C, 210D of different windows 202 and 204 is similar. As noted in FIG. 2, the data 220, 222 is generally similar throughout most of the time segments 210A, 210B, 210C, 210D. However, in time segment 210A, data 206 and 208 are substantially dissimilar. The dissimilarities may be a result of differences in the processing. The dissimilarities may also be the result of different engines, where one engine is more suited for handling an event that occurred during time segment 210A, poor signal strength during time segment 210A, an error, or the like. Thus, one feature that the patient monitor can abstract is the difference in outputs between different engines and/or different windows of time.

In an embodiment, while abstracting the data, the patient monitor compares and identifies the difference between data 206 and data 208 in time segment 210A. The patient monitor categorizes the difference depending on various factors, such as type of data being analyzed, type of analysis being performed, engines being used, etc. In an embodiment, the difference is categorized as an insignificant difference, a minor difference, and/or significant difference. Based on the categorization, the patient monitor can implement a predefined action using a look-up table, which will be described in greater detail below, with reference to FIG. 4. Additional methods for categorizing the differences between the engine outputs may be used without departing from the spirit and scope of the description. Furthermore, the categories may be encoded using any number of different bit codes, as described above.

FIG. 3 is a plot diagram illustrating another embodiment of a feature abstraction, involving a trend line, linear regression, and/or standard deviation. Graph 300 illustrates an example of data measurements 306 over time. The x-axis 302 of graph 300 represents time and the y-axis 304 represents the amplitude of the measurements 306. The line 308 represents a trend line of the data measurements 306 over time. In an embodiment, the data measurements are normalized.

In an embodiment, the patient monitor computes a confidence value of the data measurements 306. The confidence value can be computed using the standard deviation, average, correlation coefficient and/or linear regression of the data measurements 306. For example, a high standard deviation and/or low correlation coefficient may be equated with a low confidence value, whereas a low standard deviation and/or high correlation coefficient may be equated with a high confidence value. Based on the confidence value, the data can be sorted into different categories indicating the level of confidence that can be placed in the data. For example, a relatively low confidence level may indicate that the signals are experiencing relatively large amounts of noise or other distortions, and that little confidence should be placed in the output. A relatively high confidence level may indicate that the patient monitor is experiencing relatively little noise in the system, and that high confidence can be placed in the output. The categories may be implemented using bit codes, described above with reference to FIG. 1. It is to be understood that more or fewer categories can be used to categorize the standard deviation of the data, or the trend line.

Figure 4:
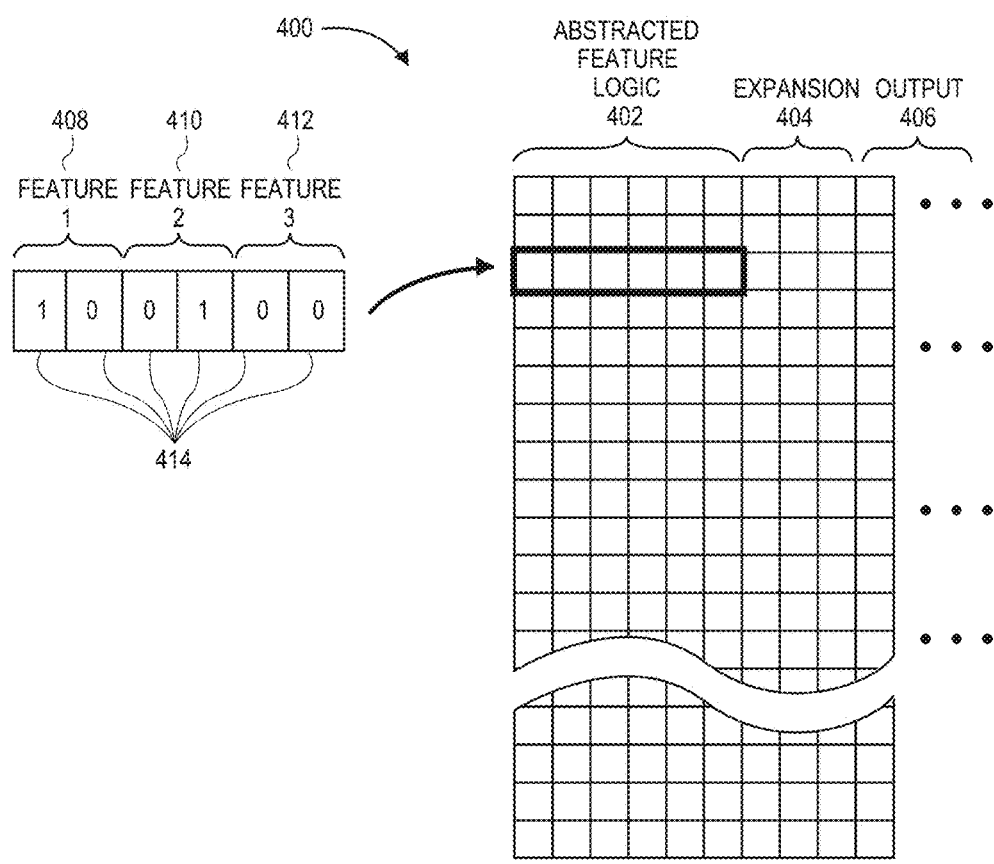
FIG. 4 is an expanded view of a lookup table that can be used by a patient monitor to determine what action to perform in view of the abstracted features.

FIG. 4 is a block diagram illustrating an embodiment of an expanded view of an electronic lookup table (LUT) 400 implemented in the patient monitor. In an embodiment, the LUT 400 includes at least three sections: the features logic section 402, the expansion section 404, and the output section 406. The features logic section 402 is further broken down into three subsections 408, 410, 412. Each subsection 408, 410, 412 includes a bit encoding of the category of one abstracted feature. Each bit encoding is made up of multiple bits and/or bytes 414. The LUT 400 can be used by the patient monitor to determine what action to perform based on the category, or bit code, of the various features of the physiological data. It will be understood that the LUT 400 is only an example, and other embodiments with fewer or more sections, subsections, bit encodings, and features may be used without departing from the spirit and scope of the description.

As mentioned, LUT 400 includes three sections: the features logic section 402, the expansion section 404, and the output section 406. The patient monitor uses the feature logic section 402 and the expansion section 404 to "lookup" the action (encoded as the output 406) that is to be performed. Thus, each possible permutation of the featured logic section 402 and the expansion section 404 can have a corresponding output section 406. In other words, the output section 406 (or action) is selected as a function of the featured logic section 402 and the expansion section 404.

The feature logic section 402 is made up of one or more subsections 408, 410, and 412. Each subsection 408, 410, 412 can include one or more representations of categories of individual features in the form of individual bits and/or bytes 414. In the example illustrated, the features logic 402 includes three subsections 408, 410, 412. Each subsection 408, 410, 412 includes a bit code, made up of two bits, for a category of one individual feature. It will be understood that the feature logic section 402 can include fewer or more subsections and that the categories of the individual features may be represented with more or fewer bits as desired. For example, a greater number of categories may be desired for some features based on their complexity. As such, the features having more categories can use larger bit codes with more bits or bytes. Accordingly, in an embodiment, the bit codes for the different features are not uniform in their size. For example, one bit code for one feature may use two bits, while another bit code for another feature may use five bytes. In another embodiment, the bit codes are uniform in size for all features.

The expansion section 404 can include a number of subsections, similar to the subsections 408, 410, 412 of the feature logic section 402. The expansion subsections can include space, in the form of bits/bytes, for new features that are not included in the subsections 408, 410, 412. When not being used, the bits/bytes in the expansion section 404 can all be set to a logic '0' or logic '1,' as desired.

As mentioned earlier, the output section 406 is used by the patient monitor to determine the appropriate action in light of the feature logic section 402 and the expansion section 404. The patient monitor can use other logic as well in determining the appropriate output or action. The output section 406 can include a number of subsections similar to the feature logic section 402 and the expansion section 404. Furthermore, the actions to be taken by the patient monitor are encoded as bit codes within the output section 406. In an embodiment, each permutation of the feature logic section 402 and the expansion section 404 equates to a different bit code in the output section 406. In another embodiment, the bit code in the output section 406 for one or more permutations of the feature logic section 402 and the expansion section 404 is the same.

By abstracting the features and using the LUT 400, the patient monitor can reduce the amount of processing resources needed to perform the appropriate action given the set of data. Rather than processing the data itself, the patient monitor is able to abstract generalizations or general characteristics of the data and make determinations based on the general characteristics themselves. Thus, the patient monitor avoids processing the individual data itself. Even in those instances where analyzing or determining a feature is resource intensive, the patient monitor is able to reduce the overall amount of processing by reducing the number of items analyzed. For instance, instead of processing hundreds or even thousands of individual pieces of data, the patient monitor is able to process all, or a large number of, the pieces of data using a relatively small number of general characteristics that apply to the pieces of data in the aggregate. In addition, the use of a lookup table allows the actions or outputs to be predetermined, allowing the patient monitor to perform a simple "lookup" rather than repeatedly determining the appropriate action for each feature or piece of data analyzed. Furthermore, the lookup table can be implemented in hardware, further saving processing resources. Another benefit of the table is that in one embodiment there are no conditions left undefined. Often, in generating large and complex if/then statements in software, conditions are inevitably left out such that the device does not know what to do under an undefined condition. The table obviates this problem by inherently providing a result for every possible state.

Figure 5:
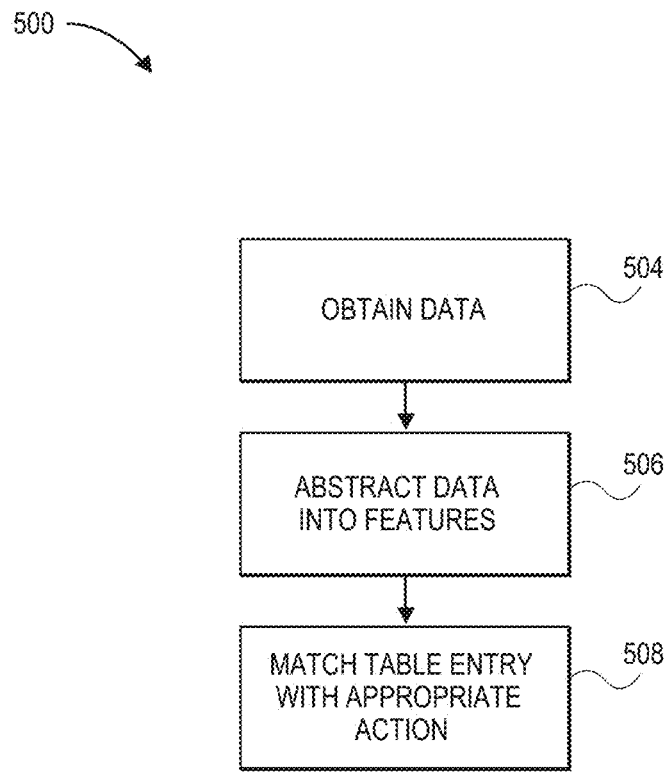
FIG. 5 is a flow chart illustrating a process implemented by a patient monitor for determining what action to perform based on the abstracted features.

FIG. 5 is a flow chart illustrating a process 500 implemented by a patient monitor for determining what action to perform based on the abstracted features. In an embodiment, the process 500 is executed in real-time or near real-time by the patient monitor. At block 504, the patient monitor obtains physiological data. The physiological data can be many various types of physiological data as described above. In some embodiments, the data need not be physiological data, as will be described in greater detail below.

At block 506, the patient monitor abstracts features of a set of data, or general characteristics. As described above, the features may include: differing engine outputs, standard deviation, slope, average, linear regression, correlation coefficient, and the like. Additional features may be used as well, such as time domain features, frequency domain features, and the like.

In abstracting the features, the patient monitor may analyze various general characteristics of the set of data in a variety of ways. For example, the patient monitor can abstract all the features or a subset of all the features. The subset can be determined based on the features that require, or are likely to use, relatively little processing resources, or can be determined randomly. In an embodiment, the patient monitor uses a list of predetermined features to determine which features to analyze. In an embodiment, the list of features is stored in the memory of the patient monitor. In another embodiment, the list is stored in memory remotely located from the patient monitor. In yet another embodiment, the patient monitor determines which features are to be abstracted based on the type of data being processed or based on the abstractions that are available to the monitor at any given point in time. For example, some features of data may be more pronounced or more easily determined based on the type of data received. For example, comparing the output of different engines of plethysmograph data may be less computationally intensive than calculating the standard deviation or linear regression of the plethysmograph data. In such an instance, the patient monitor can select to abstract the comparison between the data engines and not calculate the standard deviation or linear regression. In another embodiment, the patient monitor determines both abstractions. In an embodiment, the determination of which abstraction to use is based on a confidence level for each abstraction. In an embodiment, each abstraction is further given a confidence bit code to indicate a confidence level of that abstraction.

At block 508, the patient monitor matches the features of the set of data with an appropriate output, or action using a lookup table. The lookup table may be similar to the one described above, with reference to FIG. 4. Although not shown, the patient monitor can encode the features into different categories prior to using the lookup table. Upon completing the lookup and performing the associated action, the process 500 repeats itself as needed throughout the operation of the device.

Figure 6:
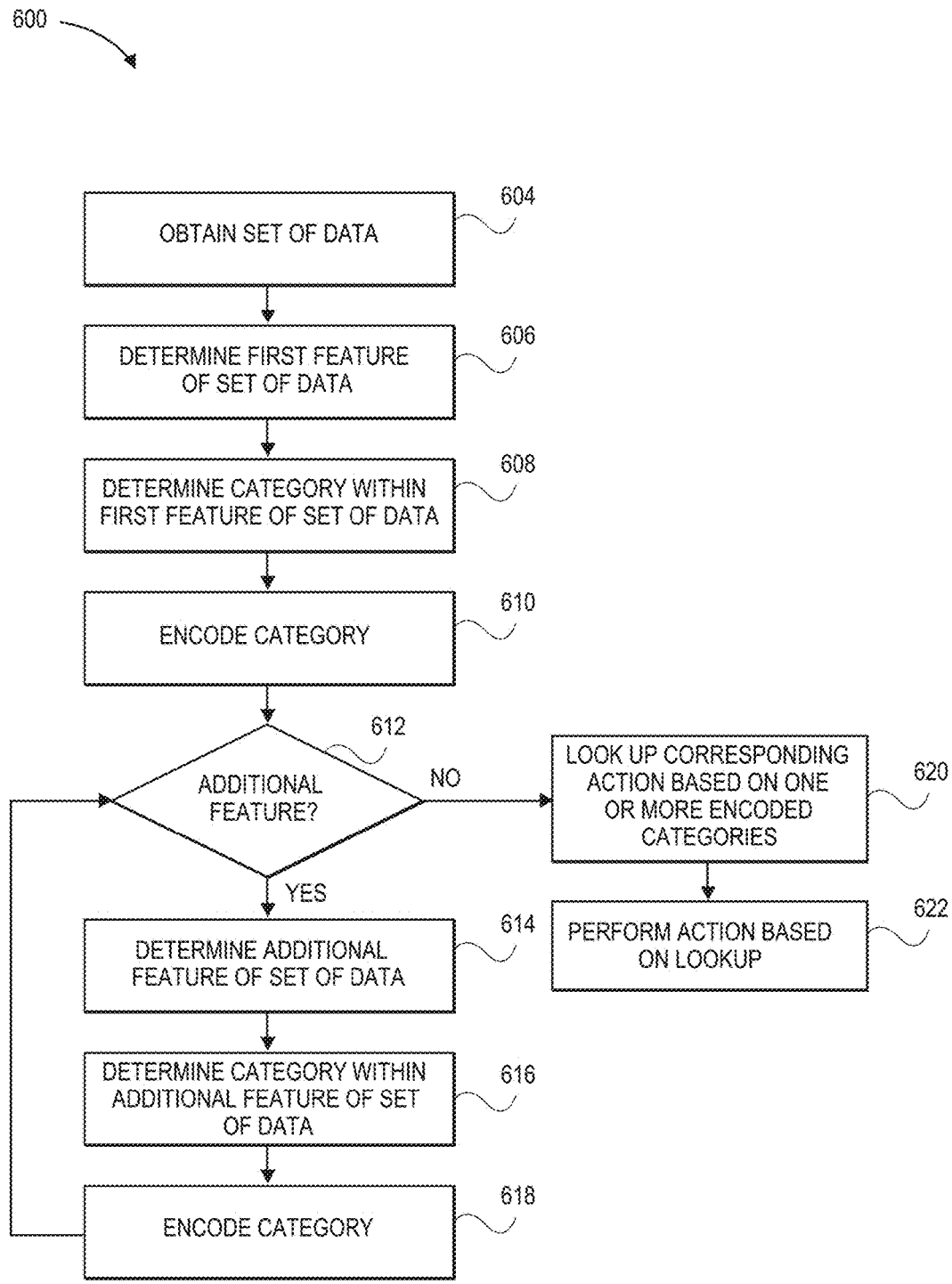
FIG. 6 is a flow chart illustrating an embodiment of a process implemented by a patient monitor for determining an appropriate action based on the features of a set of data.

FIG. 6 is a flow chart illustrating an embodiment of a process 600 implemented by a patient monitor for determining an appropriate action based on the features of physiological data, which can also be referred to as a set of data.

At block 604, the patient monitor obtains a set of data as described in greater detail above, with reference to block 502 of FIG. 5. At block 606, the patient monitor determines a first feature of the set of data. As described earlier, the feature can be any one of various general characteristics of the data including, slope, standard deviation, linear regression, correlation coefficient, differences between engine outputs, time domain, frequency domain, and the like. It is to be understood that features of data that can be abstracted are many, and should not be limited by the features specifically recited herein.

At block 608, the patient monitor determines a category within the first feature of the set of data. As described earlier, with reference to FIGS. 1, 2, and 3, the categories may take many different forms. For instance, as described above with reference to FIG. 1, if the abstracted feature is the slope of the set of data, the categories may be represented as a number of different slopes, and encoded using bit codes. Thus, the patient monitor will determine the proper slope, or category, that should be associated with the set of data.

In the example illustrated in FIG. 2, the abstracted feature is the difference between engine outputs, and the categories can be insignificant difference, minor difference, and significant difference. Thus, the patient monitor determines which category is appropriate for the difference between data 206 and 208 in time segment 210A of FIG. 2.

Similarly, the patient monitor can determine the appropriate category for the standard deviation, linear regression, correlation coefficient, and/or trend line of data measurements, as described above with reference to FIG. 3. In an embodiment, the number of different categories within a feature is finite and/or predetermined. In another embodiment, the categories are determined dynamically during process 600. In an embodiment, the categories are implemented using bit codes. In another embodiment, the categories are implemented using an alphanumeric code, or word. Furthermore, the categories of each feature may be different. For instance, one feature may have two categories and another feature may have ten or more features. Furthermore, the different categories of a feature can based on the type of data, the type of physiological data, the type of feature, the type of analysis being performed, or the like.

At block 610, the patient monitor encodes the selected category to be used when looking up the appropriate action in a lookup table. The patient monitor can encode the category in any number of different ways and use any number of different bits and/or bytes to do so. In an embodiment, the categories are represented as different sequences of bits and/or bytes, or bit codes. The patient monitor uses the bit codes to look up the appropriate output in the lookup table. Other methods of encoding the data are envisioned without departing from the spirit and scope of the description. For example, the different categories may be represented using some alphanumeric code or word, or the like.

At determination block 612, the patient monitor determines if there are additional features of the set of data to be analyzed. As described above in greater detail with reference to FIG. 4, more than one feature can be used in the lookup table to select the appropriate action. Thus, at block 612, the patient monitor determines if an additional feature of the set of data is to be analyzed. If there is an additional feature of the set of data to be analyzed, the patient monitor determines the additional feature of the set of data, as illustrated at block 614. Block 614 is similar to block 606, described above. At block 616, the patient monitor determines a category within the additional feature of the set of data, similar to block 608, described above. At block 618, the patient monitor encodes the category to use with the lookup table, as described above with reference to block 610.

After encoding the category, as illustrated at block 618, the patient monitor again determines if there is an additional feature to be analyzed, as illustrated at block 612. If there are additional features, the patient monitor continues to analyze the additional feature(s), determine the category within the additional feature(s) and encode the category, as illustrated in blocks 614, 616, and 618, respectively. Once there are no additional features, the patient monitor looks up the action corresponding to the one or more encoded categories, as illustrated at block 620.

To determine the appropriate action based on the encoded categories, the patient monitor can use a lookup table, similar to the LUT 400 described above, with reference to FIG. 4. Using the lookup table, the patient monitor can account for all of the different categories of the different features that were previously analyzed and determine the appropriate action. In an embodiment, abstracting features and using the lookup table reduces the number of computations processed by the patient monitor.

At block 622, the patient monitor performs the appropriate action based on the output of the lookup table. In an embodiment, the patient monitor repeats process 600 as desired.

It is to be understood that the different actions that can be performed by the patient monitor are many. For example, the patient monitor may determine that the appropriate action includes changing a display or output, activating an alarm, gathering additional data via the sensor, the internet or some other means, notifying a healthcare provider, the patient or another person, powering off, requesting additional information from a user, etc. Thus, the various actions that may be performed should be construed broadly.

Although described in terms of a patient monitor and physiological data, the processes described above, may be carried out using any number of general computing devices such as a personal computer, tablet, smart phone, and the like. As described above, abstracting features, or general characteristics, of data and then performing some type of action based on the general characteristics, or features, of the data rather than the data itself can significantly decrease processing resources. The process can be useful whenever abstracting and processing features would use fewer processing resources than processing the data itself or where a number of different potentials options are available and undefined states would be harmful.

For example, in an embodiment, the table of FIG. 4 can be used in conjunction with a system that automatically changes display characteristics based user proximity. In an embodiment in a system that tracks proximate users, the abstraction system described and table of FIG. 4 can be used to determine screen changes based on proximate user preferences. There can be a number of potential inputs used in determining screen orientation. These can include proximity to the screen in distance, hierarchy of proximate users, alarms relevant to proximate users, etc. Each of these inputs act as the signal abstractions and each will receive an appropriate bit code that can be used with the table of FIG. 4 to determine a solution. In an embodiment, use of the signal abstractions reduces the number nested if/then statements in software and simplifies the ability to encode for every possible solution.

Figure 7:
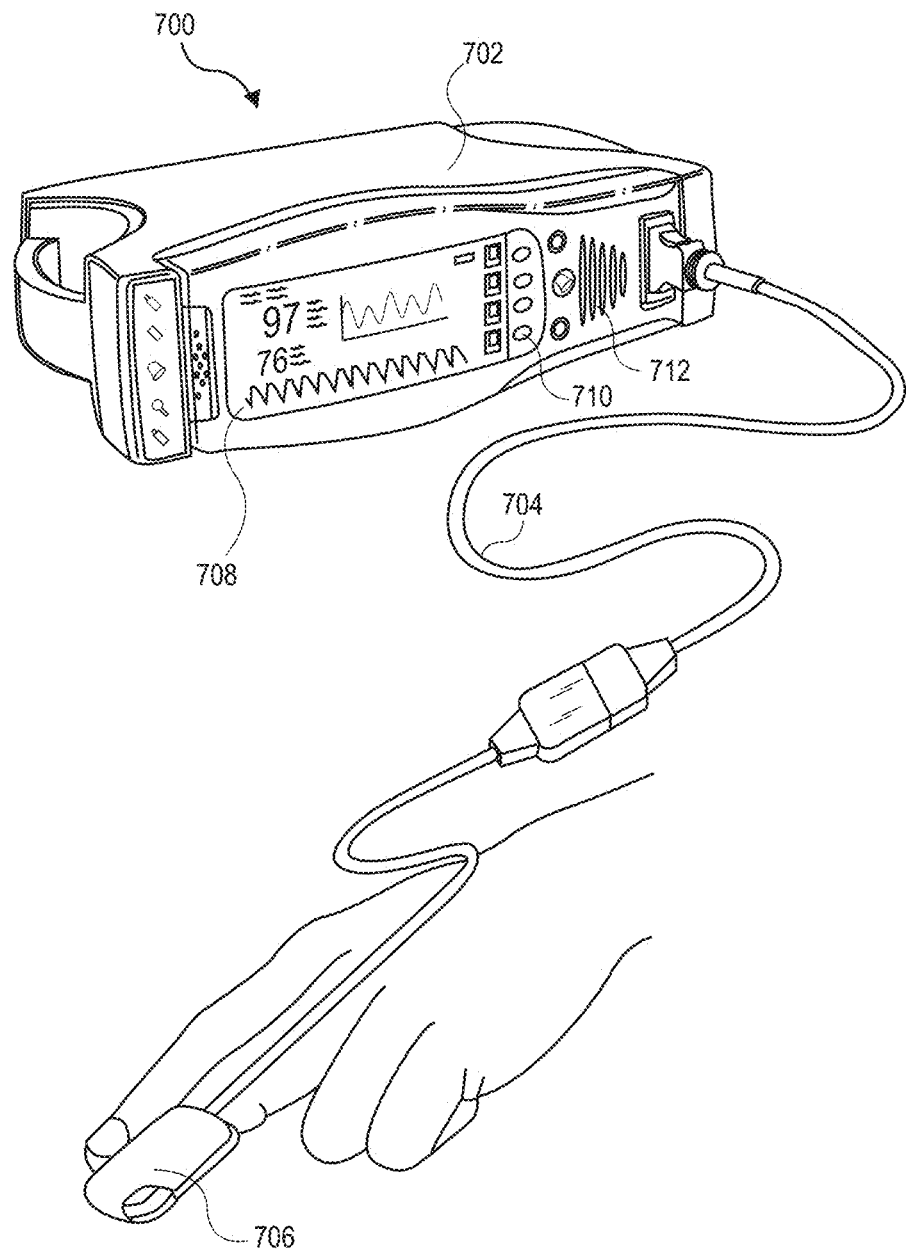
FIG. 7 illustrates an embodiment of a patient monitoring system capable of abstracting features of physiological data.

FIG. 7 illustrates an embodiment of a patient monitoring system 700 capable of abstracting features of physiological data, as described above with reference to FIGS. 1-6. The patient monitoring system 700 includes a patient monitor 702 attached to a sensor 706 by a cable 704. The sensor monitors various physiological data of a patient and sends signals indicative of the one or more parameters to the patient monitor 702 for processing.

The patient monitor 702 generally includes a display 708, control buttons 710, and a speaker 712 for audible alerts. The display 708 is capable of displaying readings of various monitored patient parameters, which may include numerical readouts, graphical readouts, and the like. Display 708 may be a liquid crystal display (LCD), a cathode ray tube (CRT), a plasma screen, a Light Emitting Diode (LED) screen, Organic Light Emitting Diode (OLED) screen, or any other suitable display. The patient monitor 702 may monitor $SpO_2$, Hb, $HbO_2$, SpHb™, SpCO®, SpOC™, SpMet®, PI, PVI®, PR, temperature, and/or other parameters.

An embodiment of a patient monitoring system 700 according to the present disclosure is capable of measuring and displaying trending data of the various parameters and preferably is capable of conducting data analysis as to the trending. Furthermore, the patient monitoring system is capable of abstracting features of the physiological data being monitored. In an embodiment, the patient monitor 702 includes an abstraction module for carrying out the processes described above. It is to be understood by one skilled in the art that the patient monitor 702 may come in various, shapes, sizes and configurations without departing from the spirit and scope of the description. For example, the patient monitor 702 may be larger, smaller, portable, comprise varying size displays 708, and the like.

The sensor 706 may be one of many different types. For example, the sensor 706 may be disposable, reusable, multi-site, partially reusable, partially disposable, be adhesive or non-adhesive, monitor the physiological parameters using reflectance, transmittance, or transreflectance, and may be placed on a finger, hand, foot, forehead, neck, or ear, and may be a stereo sensor or a two-headed sensor. Thus, one of skill in the art will appreciate that sensor 706 may be any number of different types of sensors without departing from the spirit and scope of the disclosure.

Figure 8:
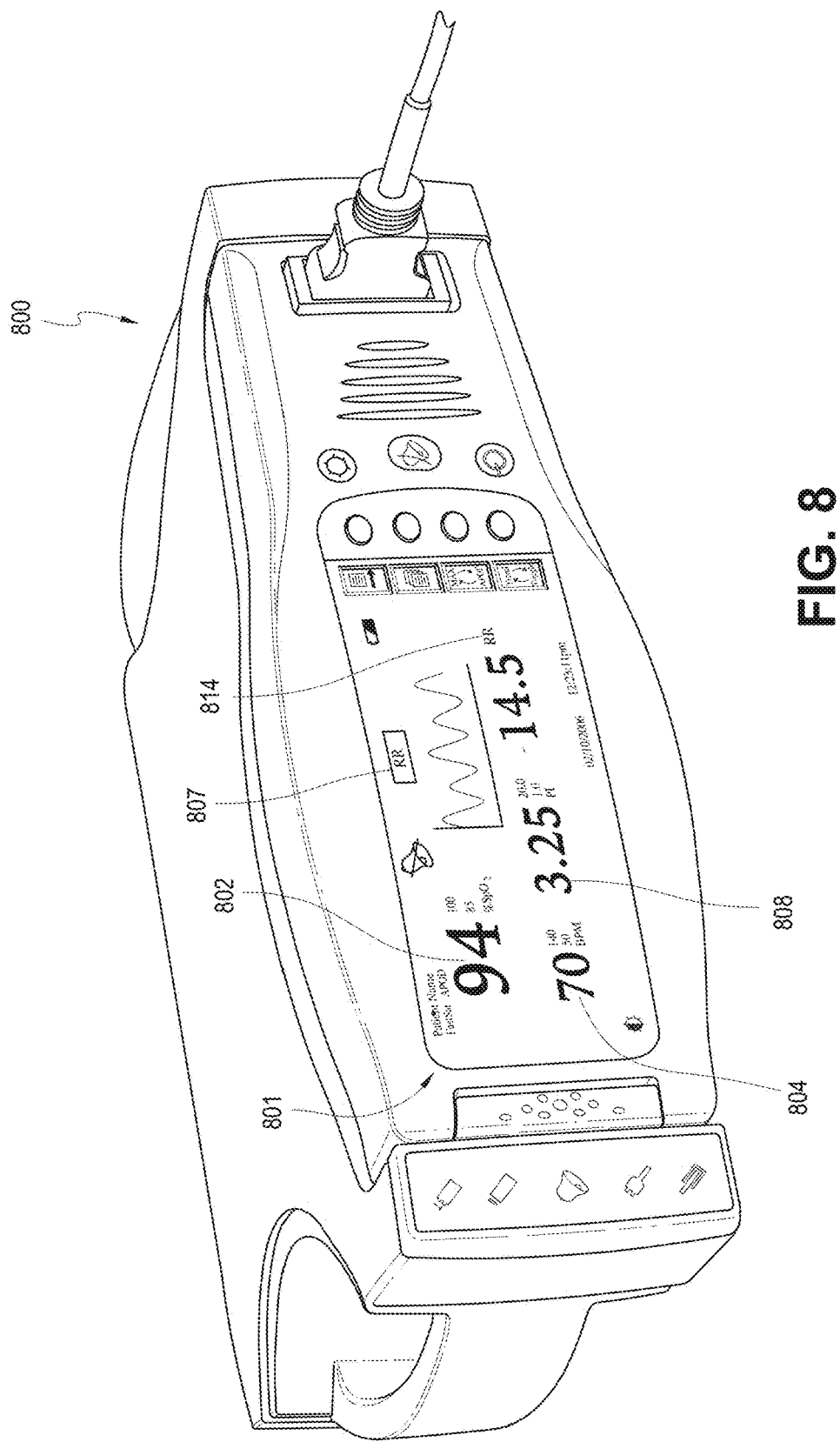
FIG. 8 illustrates an example noninvasive multiparameter physiological monitor.

FIG. 8 illustrates an example noninvasive multiparameter physiological monitor 800 that can implement any of the features, processes, steps, etc., described herein. An embodiment of the monitor 800 includes a display 801 showing data for multiple physiological parameters. For example, the display 801 can include a CRT or an LCD display including circuitry similar to that available on physiological monitors commercially available from Masimo Corporation of Irvine, Calif. sold under the name Radical™, and disclosed in U.S. Pat. Nos. 7,221,971; 7,215,986; 7,215,984 and 6,850,787, for example, the disclosures of which are hereby incorporated by reference in their entirety. In an embodiment, the multiparameter patient monitor includes an abstraction module for performing the processes described above. Many other display components can be used that are capable of displaying respiratory rate and other physiological parameter data along with the ability to display graphical data such as plethysmographs, respiratory waveforms, trend graphs or traces, and the like.

The depicted embodiment of the display 801 includes a measured value of respiratory rate 812 (in breaths per minute (bpm)) and a respiratory rate waveform graph 806. In addition, other measured blood constituents shown include $SpO_2$ 802, a pulse rate 804 in beats per minute (BPM), and a perfusion index 808. Many other blood constituents or other physiological parameters can be measured and displayed by the multiparameter physiological monitor 800, such as blood pressure, ECG readings, $EtCO_2$ values, bioimpedance values, and the like. In some embodiments, multiple respiratory rates, corresponding to the multiple input sensors and/or monitors, can be displayed.

FIG. 9 illustrates an embodiment of a sensor system 900 including a sensor assembly 901 and a monitor cable 911 suitable for use with any of the physiological monitors shown in FIGS. 7 and 8. The sensor assembly 901 includes a sensor 915, a cable assembly 917, and a connector 905. The sensor 915, in one embodiment, includes a sensor subassembly 902 and an attachment subassembly 904. The cable assembly 917 of one embodiment includes a sensor 907 and a patient anchor 903. A sensor connector subassembly 905 is connected to the sensor cable 907.

The sensor connector subassembly 905 can be removably attached to an instrument cable 911 via an instrument cable connector 909. The instrument cable 911 can be attached to a cable hub 920, which includes a port 921 for receiving a connector 912 of the instrument cable 911 and a second port 923 for receiving another cable. In certain embodiments, the second port 923 can receive a cable connected to a pulse oximetry or other sensor. In addition, the cable hub 920 could include additional ports in other embodiments for receiving additional cables. The hub includes a cable 922 which terminates in a connector 924 adapted to connect to a physiological monitor (not shown).

In an embodiment, the acoustic sensor assembly 901 includes a sensing element, such as, for example, a piezoelectric device or other acoustic sensing device. The sensing element can generate a voltage that is responsive to vibrations generated by the patient, and the sensor can include circuitry to transmit the voltage generated by the sensing element to a processor for processing. In an embodiment, the acoustic sensor assembly 901 includes circuitry for detecting and transmitting information related to biological sounds to a physiological monitor. These biological sounds can include heart, breathing, and/or digestive system sounds, in addition to many other physiological phenomena. The acoustic sensor 915 in certain embodiments is a biological sound sensor, such as the sensors described herein. In some embodiments, the biological sound sensor is one of the sensors such as those described in the '883 application. In other embodiments, the acoustic sensor 915 is a biological sound sensor such as those described in U.S. Pat. No. 6,661,161, which is incorporated by reference herein in its entirety. Other embodiments include other suitable acoustic sensors.

The attachment sub-assembly 904 includes first and second elongate portions 906, 908. The first and second elongate portions 906, 908 can include patient adhesive (e.g., in some embodiments, tape, glue, a suction device, etc.). The adhesive on the elongate portions 906, 908 can be used to secure the sensor subassembly 902 to a patient's skin. One or more elongate members 910 included in the first and/or second elongate portions 906, 908 can beneficially bias the sensor subassembly 902 in tension against the patient's skin and reduce stress on the connection between the patient adhesive and the skin. A removable backing can be provided with the patient adhesive to protect the adhesive surface prior to affixing to a patient's skin.

The sensor cable 907 can be electrically coupled to the sensor subassembly 902 via a printed circuit board ("PCB") (not shown) in the sensor subassembly 902. Through this contact, electrical signals are communicated from the multi-parameter sensor subassembly to the physiological monitor through the sensor cable 907 and the cable 911.

In various embodiments, not all of the components illustrated in FIG. 9 are included in the sensor system 900. For example, in various embodiments, one or more of the patient anchor 903 and the attachment subassembly 904 are not included. In one embodiment, for example, a bandage or tape is used instead of the attachment subassembly 904 to attach the sensor subassembly 902 to the measurement site. Moreover, such bandages or tapes can be a variety of different shapes including generally elongate, circular and oval, for example. In addition, the cable hub 920 need not be included in certain embodiments. For example, multiple cables from different sensors could connect to a monitor directly without using the cable hub 920.

Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," and U.S. Pat. Application No. 61/366,866, filed Jul. 22, 2010, entitled "Pulse Oximetry System for Determining Confidence in Respiratory Rate Measurements," the disclosures of which are hereby incorporated by reference in their entirety. An example of an acoustic sensor that can be used with the embodiments described herein is disclosed in U.S. Pat. Application No. 61/252,076, filed Oct. 15, 2009, titled "Acoustic Sensor Assembly," the disclosure of which is hereby incorporated by reference in its entirety.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The methods, steps, processes, calculations, computations or the like ("methods") provided herein are simplified examples that are generally performed by advanced processing devices, including complex signal processors, sensitive analog and digital signal preprocessing boards, optical/optoelectronic componentry, display drivers and devices, or similar electronic devices. An artisan will recognize from the disclosure herein that the various methods often must be performed at speeds that, as a practical matter, could never be performed entirely in a human mind. Rather, for many calculations providing real time or near real time solutions, outputs, measurements, criteria, estimates, display indicia, or the like, many of the foregoing processing devices perform tens to billions or more calculations per second. In addition, such processing devices may process electrical signals, infrared signals, wireless signals, or other electromagnetic wave signals that are incomprehensible to a human mind in their raw form and at the speeds communicated.

The various illustrative logical blocks, modules, circuits, and algorithm steps described in connection with the embodiments disclosed herein can be implemented as electronic hardware, computer software, or combinations of both operating in real-time or near real-time and at speeds unattainable by a human. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method for reducing processing load of a patient monitor in communication with a physiological sensor, the physiological sensor configured to emit light towards a tissue site, detect the light after it has been attenuated by tissue, and output a signal responsive to the detected light, the method comprising:

receiving, at the patient monitor, the signal from the physiological sensor, wherein the signal corresponds to physiological data and comprises a plurality of features including at least a first feature and a second feature;

associating a category of a first set of categories with the first feature;
associating a category of a second set of categories with the second feature;
determining an action from a set of actions to perform based at least in part on a combination of at least a first value corresponding to the category associated with the first feature and a second value corresponding to the category associated with the second feature; and
causing the determined action to be performed.

2. The method of claim 1, wherein said associating the category of the first set of categories with the first feature is based at least in part on an identification of which category of the first set of categories most closely corresponds to the first feature.

3. The method of claim 1, further comprising determining a confidence value based at least in part on the first feature, wherein said associating the category of the first set of categories with the first feature is based at least in part on the confidence value.

4. The method of claim 1, wherein at least one of the first feature or the second feature comprises at least one of a trend line corresponding to the signal, a standard deviation corresponding to the signal, a slope corresponding to the signal, a change in the slope corresponding to the signal, a correlation coefficient corresponding to the signal, or a linear regression corresponding to the signal.

5. The method of claim 1, wherein the action from the set of actions includes at least one of changing a display of the patient monitor, changing an output of the patient monitor, activating an alarm, receiving one or more additional signals from the physiological sensor, receiving additional data via a network, powering off the patient monitor, or requesting additional information from a user.

6. The method of claim 1, wherein said determining the action from the set of actions is further based at least in part on an aggregation of at least the first value and the second value.

7. The method of claim 1, wherein the plurality of features are predetermined.

8. The method of claim 7, further comprising selecting the first feature, the second feature, or both based at least in part on a data type of the signal.

9. The method of claim 7, wherein the physiological sensor comprises a pulse oximetry sensor or an acoustic sensor.

10. The method of claim 1, further comprising selecting the first feature and the second feature from a predetermined set of features, wherein determining the first feature or the second feature uses fewer processing resources than determining other features of the predetermined set of features would use, wherein the predetermined set of features is a subset of the plurality of features.

11. The method of claim 1, wherein at least one of the category of the first set of categories or the category of the second set of categories comprises a bit code, a sequence of bits, a sequence of bytes, or an alphanumeric code.

12. A patient monitoring system comprising:
one or more processors in communication with a physiological sensor that is configured to emit light towards a tissue site, detect the light after it has been attenuated by tissue, and output a signal responsive to the detected light, the one or more processors configured to:
receive the signal from the physiological sensor, wherein the signal corresponds to physiological data and comprises a plurality of features including at least a first feature and a second feature,
associate a category of a first set of categories with the first feature and a category of a second set of categories with the second feature,
determine an action from a set of actions to perform based at least in part on a combination of at least a first value corresponding to the category associated with the first feature and a second value corresponding to the category associated with the second feature, and
cause the determined action to be performed.

13. The system of claim 12, wherein to associate the category of the first set of categories with the first feature, the one or more processors are further configured to determine which category of the first set of categories most closely corresponds to the first feature.

14. The system of claim 12, wherein the one or more processors are further configured to determine a confidence value associated with the signal based at least in part on at least one of the first feature or the second feature, wherein to associate the category of the first set of categories with the first feature, the one or more processors associate the category of the first set of categories with the first feature based at least in part on the confidence value.

15. The system of claim 12, wherein the first feature or the second feature comprises one or more of a tread line corresponding to the signal, a standard deviation corresponding to the signal, a slope corresponding to the signal, a change in the slope corresponding to the signal, a correlation coefficient corresponding to the signal, or a linear regression corresponding to the signal.

16. The system of claim 12, wherein the action from the set of actions comprises at least one of changing a display of a patient monitor, changing an output of the patient monitor, activating an alarm, receiving additional data from the physiological sensor, receiving additional data via a network, powering off the patient monitor, or requesting additional information from a user.

17. The system of claim 12, wherein the one or more processors are further configured to select the first feature and the second feature from a predetermined set of features, wherein a determination of the first feature or the second feature uses fewer processing resources than a determination of other features of the predetermined set of features would use, wherein the predetermined set of features is a subset of the plurality of features.

18. The system of claim 12, wherein the one or more processors are further configured to further select the first feature, the second feature, or both based at least in part on a data type of the signal.

19. The system of claim 12, wherein at least one of the category of the first set of categories or the category of the second set of categories comprises a bit code, a sequence of bits, a sequence of bytes, or an alphanumeric code.

20. A computer-implemented method for reducing processing load of a patient monitor, the method comprising:
under control of one or more computing devices of the patient monitor:
receiving, at a patient monitor, a signal from a physiological sensor, wherein the signal corresponds to physiological data and comprises a plurality of features including at least a first feature and a second feature;
associating a category of a first set of categories with the first feature and a category of a second set of categories with the second feature;
determining an action from a set of actions to perform based at least in part on a aggregation of at least a first value corresponding to the category associated with the first feature and a second value corresponding to the category associated with the second feature; and
causing the determined action to be performed.

\* \* \* \* \*